US00PP09189P

United States Patent [19]

Dehan

[11] Patent Number: Plant 9,189

[45] Date of Patent: Jul. 4, 1995

[54] IMPATIENS PLANT NAMED 'DEBKA'

[75] Inventor: Klara Dehan, Holon, Israel

[73] Assignee: Danziger "Dan" Flower Farm, Moshav Maishmar Hashiva, Israel

[21] Appl. No.: 315,779

[22] Filed: Sep. 30, 1994

[51] Int. Cl.[6] ..... A01H 5/00

[52] U.S. Cl. ..... Plt./87.6

[58] Field of Search ..... Plt. 87.6

*Primary Examiner*—James R. Feyrer

[57] ABSTRACT

A distinct cultivar of Impatiens plant named Debka, characterized by its large and round purple-violet flowers; freely branching habit; spreading and compact growth habit; dark green and glossy non-variegated foliage; and medium leaf size.

1 Drawing Sheet

The present invention relates to a new and distinctive cultivar of New Guinea Impatiens, botanically known as *Impatiens hawkeri,* and hereinafter referred to by the cultivar name Debka.

The new cultivar was developed by me in a controlled breeding program at Danziger—"Dan" Flower Farm, Mishmar Hashiva, Israel, by crossing the female, or seed, parent identified as *Impatiens hawkeri* selection DAN 7-87 with the male, or pollen, parent identified as *Impatiens hawkeri* selection DAN 5-53. Both parents are nonpatented selections developed by me in a controlled breeding program and used only as breeding parents.

Asexual reproduction of the new cultivar by terminal cuttings taken by me at Mishmar Hashiva, Israel, has shown that the combination of features of this new Impatiens are firmly fixed and retained through successive generations of asexual reproduction.

The following characteristics are repeatedly observed and are determined to be the distinctive and unique characteristics of Debka. These characteristics in combination distinguish Debka from both its parent varieties and other cultivated New Guinea Impatiens used in the floriculture industry:

1. Large and round purple-violet flowers.
2. Freely branching habit.
3. Compact and spreading growth habit.
4. Dark green and glossy non-variegated foliage.
5. Medium leaf size.

The new cultivar is most similar to the patented *Impatiens hawkeri* cultivar Danserra (U.S. Plant Pat. No. 8,264) in flower color. However Debka differs from Danserra in its more compact growth habit, increased branching, and darker and glossier leaf color compared to Danserra.

The accompanying colored photograph illustrates the overall appearance and flower color of the new cultivar, showing the colors as true as it is reasonably possible to obtain in colored reproductions of this type. The flower color in the photograph is more red than the actual flower color. The photograph constitutes a top perspective view of a typical potted plant of Debka.

In the following description, color references are made to The Royal Horticultural Society Colour Chart except where general terms of ordinary dictionary significance are used. The following observations, measurements and comparisons describe plants grown in Mishmar Hashiva, Israel, under normal commercial practice in a polyethylene-covered greenhouse with minimum temperatures of 12° to 14° C. during the winter and maximum temperatures of 35° C. during the summer. Average light level in the greenhouse is 40,000 lux. Debka has not been observed under all possible environmental conditions. The phenotype may vary significantly with variations in environment such as temperature, light intensity and daylength.

Botanical classification: *Impatiens hawkeri* cultivar Debka.

Parentage:

*Female (seed) parent.*—*Impatiens hawkeri* DAN 7-87.

*Male (pollen) parent.*—*Impatiens hawkeri* DAN 5-53.

Propagation:

A. *Type.*—Terminal tip cuttings.

B. *Time to initiate roots.*—1. Summer: 7 days at 25° C. 2. Winter: 9 days at 20° C.

C. *Rooting habit.*—Fibrous and well-branched.

Plant description:

A. *General apperance.*—Freely branching, spreading and compact growth habit; suitable for 10 cm pots and hanging baskets.

B. *Foliage description.*—1. Shape: Lanceolate with acuminate tip and attenuate base. 2. Size: a. Length: 8.5 cm. b. Width: 3.5 cm. 3. Texture: Smooth and very glossy. 4. Margin: Finely serrated. 5. Color: a. Young foliage, upper surface: 147A. b. Young foliage, under surface: 138B. c. Mature foliage, upper surface: 147A. d. Mature foliage, under surface: 138B. e. Veins, upper surface: 147C. f. Veins, under surface: 147C.

C. *Stem description.*—1. Internode length: 3 cm. 2. Stem color: 146B.

Flowering description:

A. *Flowering habit.*—Freely flowering.

B. *Natural flowering season.*—Year-round. Early flowering: under summer conditions, plants flower 8 to 9 weeks after planting; and under winter conditions, plants flower 12 to 13 weeks after planting.

C. *Flowers borne.*—Flower buds develop in leaf axils. Open flowers are displayed above the foliage.

D. *Quantity of inflorescences.*—Very floriferous; usually 2 flowers per axil and about 10 flowers per lateral branch at various stages of development; usually 4 fully open flowers per lateral branch.

E. *Flower opening rate.*—From bud initiation, flowers are fully open after 5 to 10 days depending on temperature, humidity and light level.

F. *Flower size.*—1. Length: 6 cm. 2. Width: 6 cm.

G. *Petals.*—1. Shape: Cordate. 2. Quantity: 5. 3. Color: a. When opening: 78A. b. Upper surface: 78A. c. Upper surface: 78A. d. Fading to: 78D.

H. *Flower bud.*—1. Shape: Round with spur. 2. Color: 72B.

I. *Spur.*—1. Shape: Needle-shaped, curved at end. 2. Color: 184B. 3. Length: a. On flower bud 2.7 cm. b. On opened flower: 3.8 cm.

J. *Reproductive organs.*—1. Androecium: a. Stamen number: 5. b. Anther shape: Oblong. c. Anther color: 75D. d. Pollen color: 155D. 2. Gynoecium: a. Stigma color: 143A. b. Style color: 143A. c. Ovary: Superior, 5-celled. d. Ovary color: 143A. e. Ovary size: 1 to 2 mm.

Disease resistance: No fungal or bacterial problems observed.

Seed development: Seed production is very rarely observed.

I claim:

1. A new and distinct cultivar of Impatiens plant named Debka, as illustrated and described.

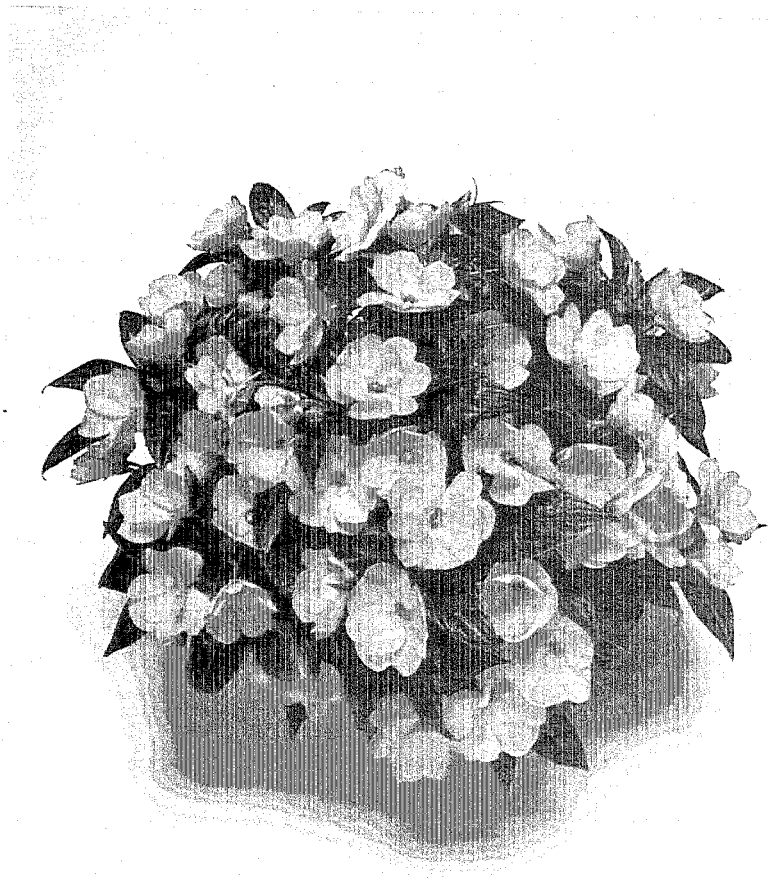

* * * * *